United States Patent [19]

Tunc

[11] Patent Number: 4,539,981

[45] Date of Patent: Sep. 10, 1985

[54] ABSORBABLE BONE FIXATION DEVICE

[75] Inventor: Deger C. Tunc, East Brunswick, N.J.

[73] Assignee: Johnson & Johnson Products, Inc., New Brunswick, N.J.

[21] Appl. No.: 439,962

[22] Filed: Nov. 8, 1982

[51] Int. Cl.³ .................. A61F 5/04; A61B 17/04
[52] U.S. Cl. ................. 128/92 B; 128/334 R; 128/92 C; 623/16
[58] Field of Search ............ 128/334 R, 1 R, 92 C, 128/92 B, 335.5; 3/1, 1.9, 1.4; 528/354; 424/78

[56] References Cited

U.S. PATENT DOCUMENTS

| | | | |
|---|---|---|---|
| 2,703,316 | 3/1955 | Schneider | 260/78.3 |
| 3,773,919 | 11/1973 | Boswell | 424/19 |
| 3,982,543 | 9/1976 | Schmitt et al. | 128/335.5 |
| 4,141,087 | 2/1979 | Shalaby et al. | 128/334 R |
| 4,265,247 | 5/1981 | Lenz et al. | 128/335.5 |
| 4,379,138 | 4/1983 | Pitt et al. | 128/92 B |

FOREIGN PATENT DOCUMENTS 1254015  2/1960  France .
1425333  11/1964  France .

*Primary Examiner*—Richard J. Apley
*Assistant Examiner*—David Isabella
*Attorney, Agent, or Firm*—Michael O. Tatlow

[57] ABSTRACT

An absorbable internal bone fixation device is disclosed. The device is made from a high molecular weight polymer of L(—)lactide having an inherent viscosity above 4.5. The polymer contains less than 2% unreacted monomer and is polymerized under conditions of selected monomer to catalyst ratios and temperatures.

7 Claims, 7 Drawing Figures

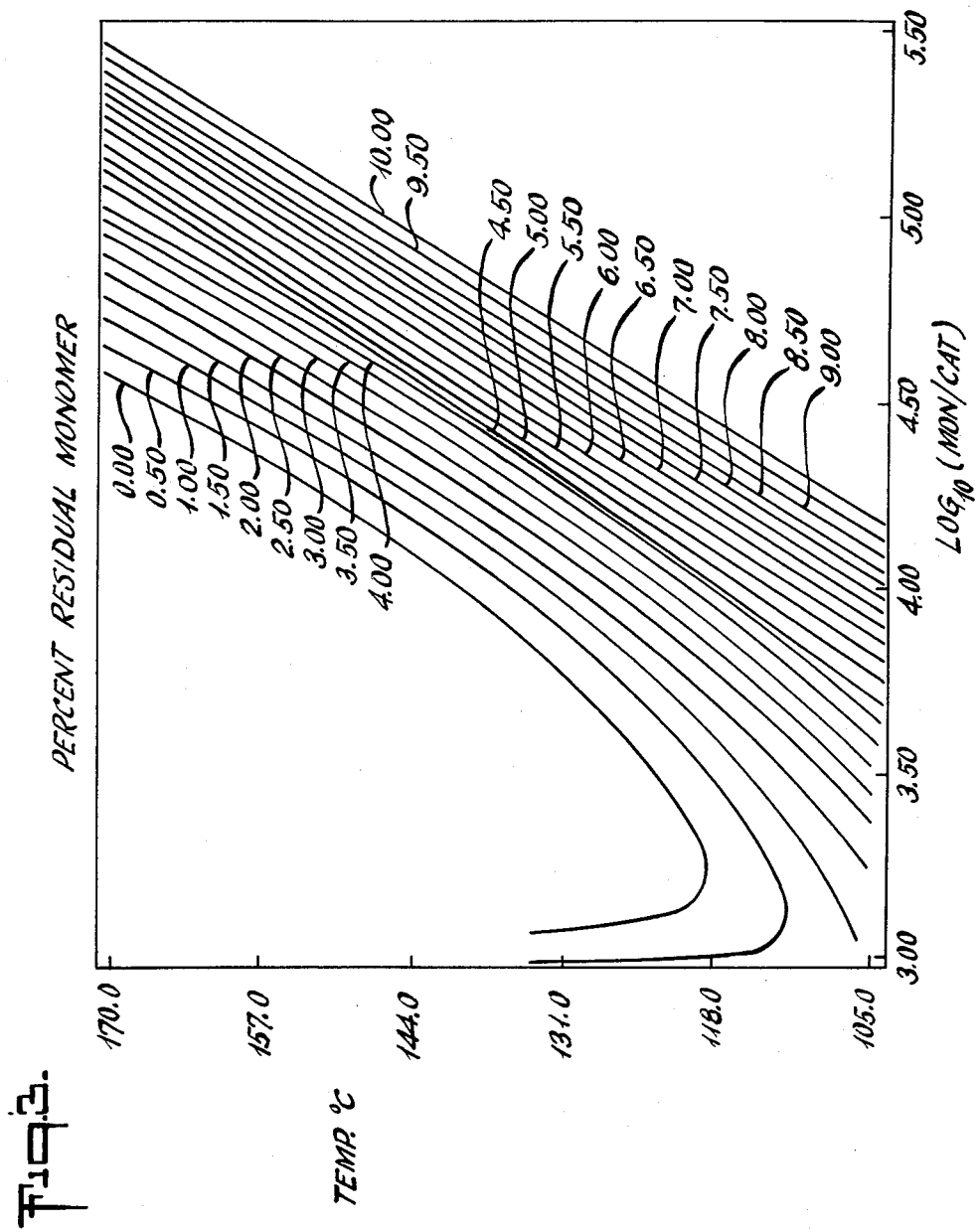

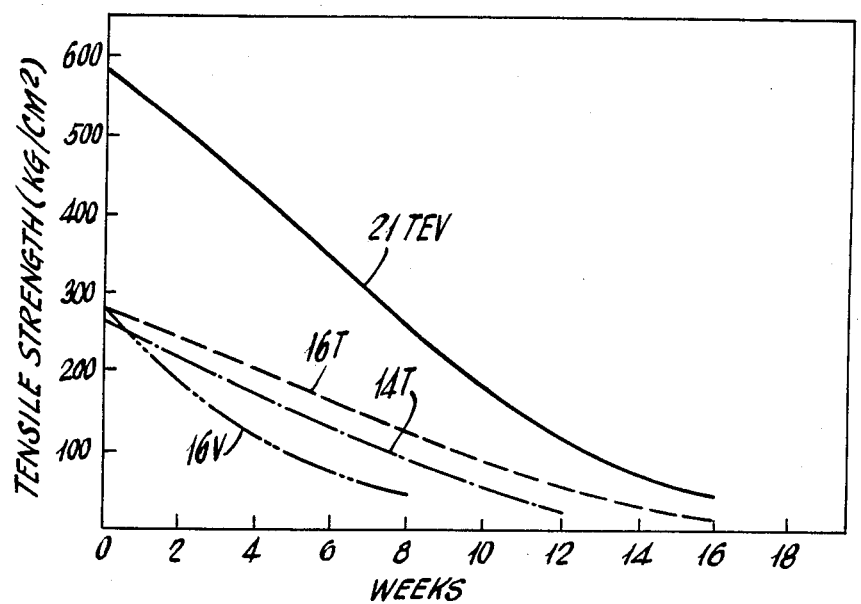
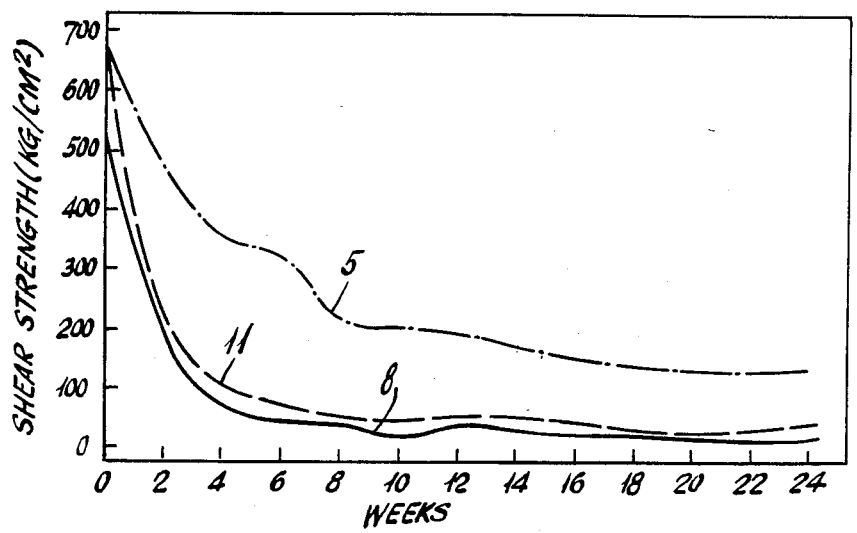

ABSORBABLE BONE FIXATION DEVICE

BACKGROUND OF THE INVENTION

1. Field of the Invention

This invention relates to internal bone fixation devices which are made of very high molecular weight polymers of L(−)lactide. These devices are absorbable in the human body and need not be removed after the bone has healed.

2. Prior Art

Presently available bone fixation devices are made of metals. These metal devices are employed in severe bone fractures where it is necessary to secure the ends of the fractured bones in proximity of each other so that they may properly heal. These devices are generally in the form of intramedullary rods and pins and plates and screws. The major problem with such metal bone fixation devices is the desirability, if not necessity, of removing the devices after the bone has completely healed. The surgical procedure necessary for the removal of such devices results in additional trauma to the patient as well as increased medical costs.

It has been previously suggested that internal bone fixation devices be made of a synthetic absorbable polymer which would eliminate the necessity of the second surgical procedure to remove such fixation devices. U.S. Pat. Nos. 3,463,158; 3,636,956; 3,739,773; 3,797,499 and 3,839,297 disclose or suggest bone fixation devices made from synthetic polymers which are either polylactides, polyglycolides or copolymers of lactide and glycolide. However, prostheses made according to the teachings of these patents have been found not to have adequate load-bearing strength for the length of time that is necessary to allow their utilization as internal bone fixation devices. These prior art polymers did not maintain adequate strength for a sufficient length of time to provide the necessary load-bearing strength until the fractured bones had properly healed and could assume their normal load-bearing function.

It is believed that the polymers disclosed in the prior art were not of sufficiently high molecular weight to allow them to retain strength over the required time period, and they began to degrade and to be absorbed in the body before the bone was adequately healed and capable of assuming the normal load-bearing function.

SUMMARY OF THE INVENTION

The bone fixation devices of the present invention may be in the form or configuration that are usually employed as metal bone fixation devices. These are plates which are used to secure a fracture in proximity so that it may be healed, screws which are used to affix the plates to the bones, wires, rods, pins, staples, cable ties and clips. The particular configuration of the bone fixation devices is not a part of the present invention. The devices made from the polymer disclosed herein are generally identical in their configuration as such devices made from metal but may be of somewhat greater thickness then the metal device.

The present bone fixation devices are made from a polymer of L(−)lactide, which polymer has an extremely high molecular weight as indicated by its inherent viscosity. The devices made from such polymers will maintain load-bearing strength after implantation for a sufficient period of time for the bone to heal and assume its load-bearing capability.

The inherent viscosity of the present L(−)lactide polymers is between 4.5 and 10. Generally, these polymers have a weight average molecular weight in excess of one million. However, the molecular weight of the polymers is difficult to accurately determine, and inherent viscosity is used herein as a more reliable technique to characterize the molecular weight of the polymer.

In addition to a high inherent viscosity, the solid polymer from which the devices of the present invention are fabricated must also have a low unreacted monomer content. The presence of unreacted monomer in the devices caused rapid degradation of the polymer with the resulting rapid loss in the required strength properties of the bone fixation devices. The unreacted monomer content in the polymer must be below about 2%, and preferably below 1%, and most preferably at 0% or below the limits of detectability.

In order to obtain the polymer with the necessary properties, the conditions of polymerization must be very carefully controlled as will be hereafter explained in greater detail. Generally, the monomer to catalyst ratio and the temperature of the polymerization reaction are interdependent and must be controlled to produce a polymer with the desired properties.

DESCRIPTION OF THE DRAWINGS

FIG. 3 is a graph plotting the monomer content of polymers produced under different reaction conditions.

FIG. 4 is a graph plotting the loss of tensile strength with time of various lactide polymers.

FIG. 5 is a graph plotting the loss of shear strength with time of various lactide polymers.

DETAILED DESCRIPTION OF THE INVENTION

Figure 1:
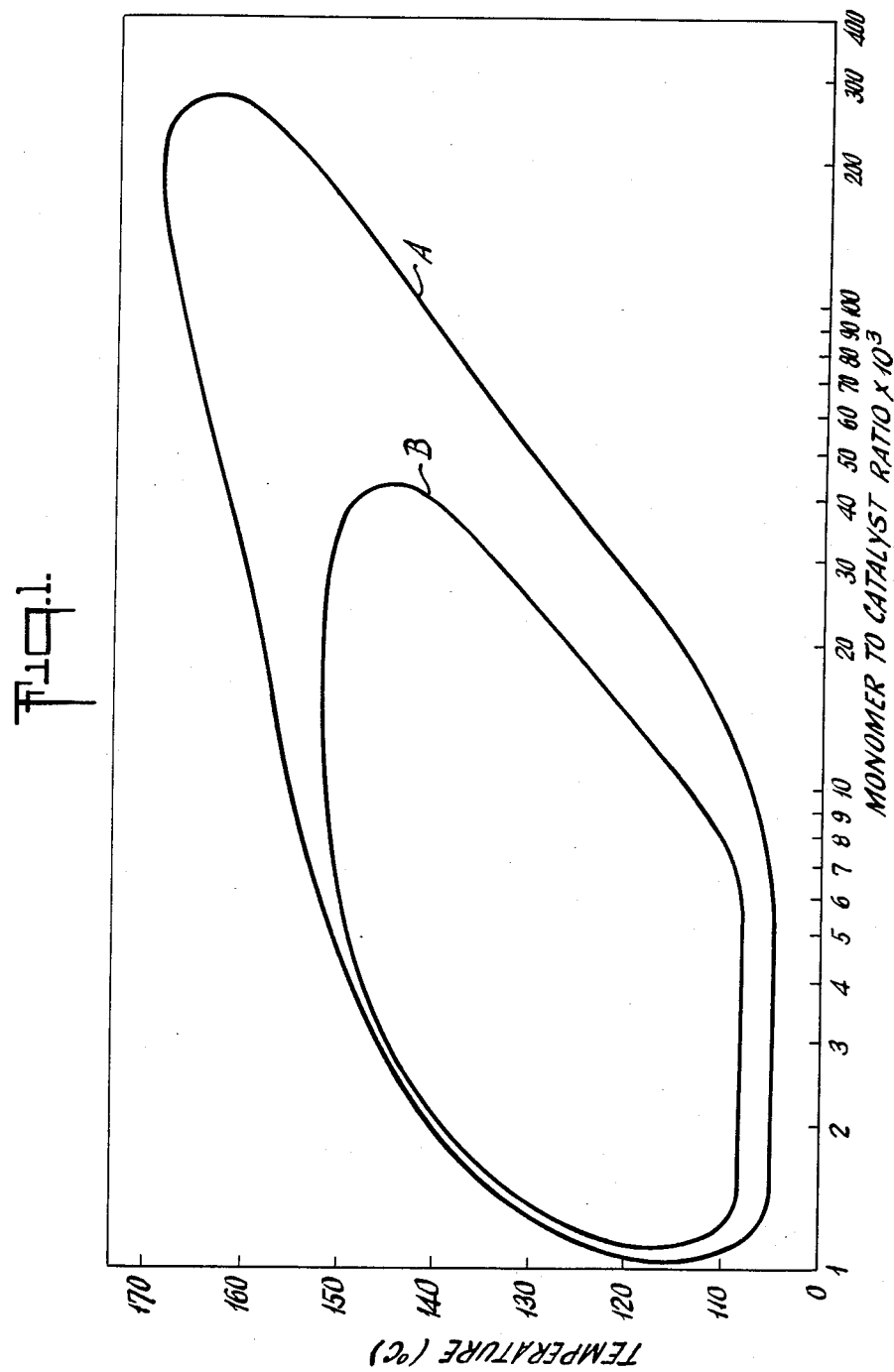
FIG. 1 is a semi-log graph depicting the relationship between the monomer to catalyst ratio and the polymerization temperature showing within the enclosed areas the reaction conditions producing suitable polymers.

The absorbable bone fixation devices of the present invention are polymers of L(−)lactide. The recurring unit in the polymer may be depicted by the general formula:

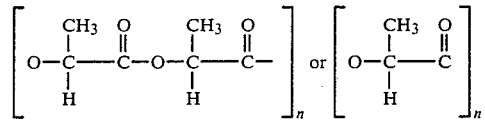

The lactide monomer must be free of impurities and free of moisture in order to obtain suitable polymers.

The bone fixation devices of the present invention have a tensile strength of at least 500 kilograms per square centimeter before implantation. After the devices are implanted, the polymer from which the devices are made will begin to degrade by hydrolysis and be absorbed by the body. As the polymer degrades, the device will lose its tensile strength. In order to be useable, the device must maintain its strength for a sufficient time for the bone to begin to heal and assume some portion of the load-bearing requirements. Generally, the tensile strength and the shear strength of the implant, eight weeks after implantation, should be at least 100 kilograms per square centimeter. In order to meet these requirements, the polymers from which the devices are made must have a very high molecular weight. The inherent viscosity of the polymers, which is an indication of molecular weight, should be greater than 4.5 and preferably between 7 and 10 in order to meet the requirements set forth above. Polymers with inherent viscosities between 4.5 and 7 may be used in some applications such as finger, wrists and other applications where there are relatively low load-bearing requirements. Polymers with inherent viscosities lower than 4.5 may be acceptable for other surgical uses, such as in sutures or in vascular grafting material, but are of insufficient viscosity to provide an absorbable bone fixation device which will maintain load-bearing strength for the required length of time.

In order to obtain polymers of the above-indicated inherent viscosity, it is necessary that the reaction conditions for the polymerization be critically controlled. As previously indicated, the resulting polymers must also have very low residual unreacted monomer content. By a very low residual monomer content it is preferred that the resulting solid polymers have a monomer content of less than one percent (1%) based on the total weight of the reaction product of the polymerization, although a monomer content of between 1% and 2% will be acceptable for some devices. The catalyst that is used in the polymerization of the polymers of the present invention has been known to catalyze the present monomers. The preferred catalyst is stannous octoate. In the process of producing the polymers of the present invention, however, the amount of catalyst, as measured by the mole ratio of the monomer to the catalyst must be controlled in conjunction with the control of the reaction temperature of the polymerization. Generally, the monomer to catalyst ratio is between 1,000 and 300,000, and the preferred ratio is between 1,100 and 45,000 and the most preferred ratio being between 1,300 and 20,000. The polymerization is maintained at a reaction temperature of 105°–150° C., and preferably between 105°–155° C., and most preferably between 110°–130° C. It is, however, necessary to maintain the monomer to catalyst ratio in conjunction with the particular reaction temperature selected. That is, a high monomer to catalyst ratio with a reaction temperature at the lower end of the above range would result in high levels of unreacted monomer and an unacceptable polymer for the purposes of the present invention. A high monomer to catalyst ratio with too high a temperature would result in an extremely low molecular weight polymer, which is also unsuitable in manufacturing the bone fixation devices of the present invention. A low monomer to catalyst ratio and a temperature at the lower end of the above scale results in nonuniform and thermally unstable polymers, which are also unsuitable for the present purposes. It is, therefore, necessary to maintain the ratio of monomer to catalyst in a range which is suitable for the particular temperature at which the polymerization reaction occurs.

Although stannous octoate is the preferred catalyst, other catalysts such as antimony triflouride, powdered zinc, dibutyl tin oxide and stannous oxalate may also be used to produce the high molecular weight polymers of the present invention.

The polymer of the present invention is preferably made from 100% L(−)lactide monomer. However, minor amounts, i.e., 10% or less, of compatible comonomers may be polymerized with the L(−)lactide. Suitable comonomers include:
beta-propiolactide
tetramethylglycolide
beta-butyrolactone
gamma-butyrolactone
pivalolactone
alpha-hydroxyacetic acid
alpha-hydroxybutyric acid
alpha-hydroxyisobutyric acid
alpha-hydroxyvaleric acid
alpha-hydroxyisovaleric acid
alpha-hydroxycaproic acid
alpha-hydroxyisocaproic acid
alpha-hydroxy-alpha-ethylbutyric acid
alpha-hydroxy-beta-methylvaleric acid
alpha-hydroxyheptanoic acid
alpha-hydroxyoctanoic acid
alpha-hydroxydecanoic acid
alpha-hydroxymyristic acid
alpha-hydroxystearic aicd In addition to the requirement that the polymers have a high molecular weight, the solid polymers must also have a very low residual unreacted monomer content. The presence of unreacted monomer in the polymer causes a more rapid degradation of the polymer in the body than if small amounts or no monomer is present. The solid polymer should contain less than 2%, based on the weight of the polymer, and preferably less than 1%.

In addition to controlling the monomer to catalyst ratio and the reaction temperature, it is also necessary to control any moisture that may be contained in the lactide monomer. This can be accomplished by thoroughly drying the monomer before the polymerization is initiated.

Generally the process of preparing the polymers of the present invention includes charging the monomer and the proper amount of catalyst into a glass reactor under dry conditions, such as under a flow of dry nitrogen in a glovebox. The glass reactor is then evacuated for 15 minutes at extremely low pressures, such as 0.02 millimeters of mercury. The reactor is then refilled with dry nitrogen, and the evacuation is repeated twice. After the flask reactor is evacuated for the third time, it is sealed. The polymerization is then carried out in a controlled temperature oil bath while the contents of the reactor are magnetically stirred. As the polymerization proceeds, the viscosity of the reaction product increases until the point is reached that the magnetic stirrer can no longer be turned. At this point, the stirrer is shut off and the reaction is continued. Generally, the reaction time, in order to produce a polymer having the stated characteristics, is between 50 and 120 hours. After the reaction is completed, the solid polymer is removed from the reaction vessel and is machined using ordinary machine tools or the polymer is ground and molded to form the desired fixation device which would be used for implantation.

The polymerization reaction conditions necessary to produce an acceptable polymer are depicted in FIG. 1 which plots reaction temperature in degrees Celsius versus monomer to catalyst ratio $\times 10^3$ on a semi-log scale. The area within the enclosed curve A are those reaction conditions which will result in the high inherent viscosity, low monomer content polymers which are generally suitable for absorbable bone fixation devices. The area within the enclosed curve B are those reaction conditions which will result in the preferred polymers and those polymers which have the most desired in vivo properties and are capable of maintaining load-bearing properties for extended periods of time. These polymers can be used to fabricate fixation devices for use in high load-bearing applications such as the bones in the arms and legs.

Figure 2:
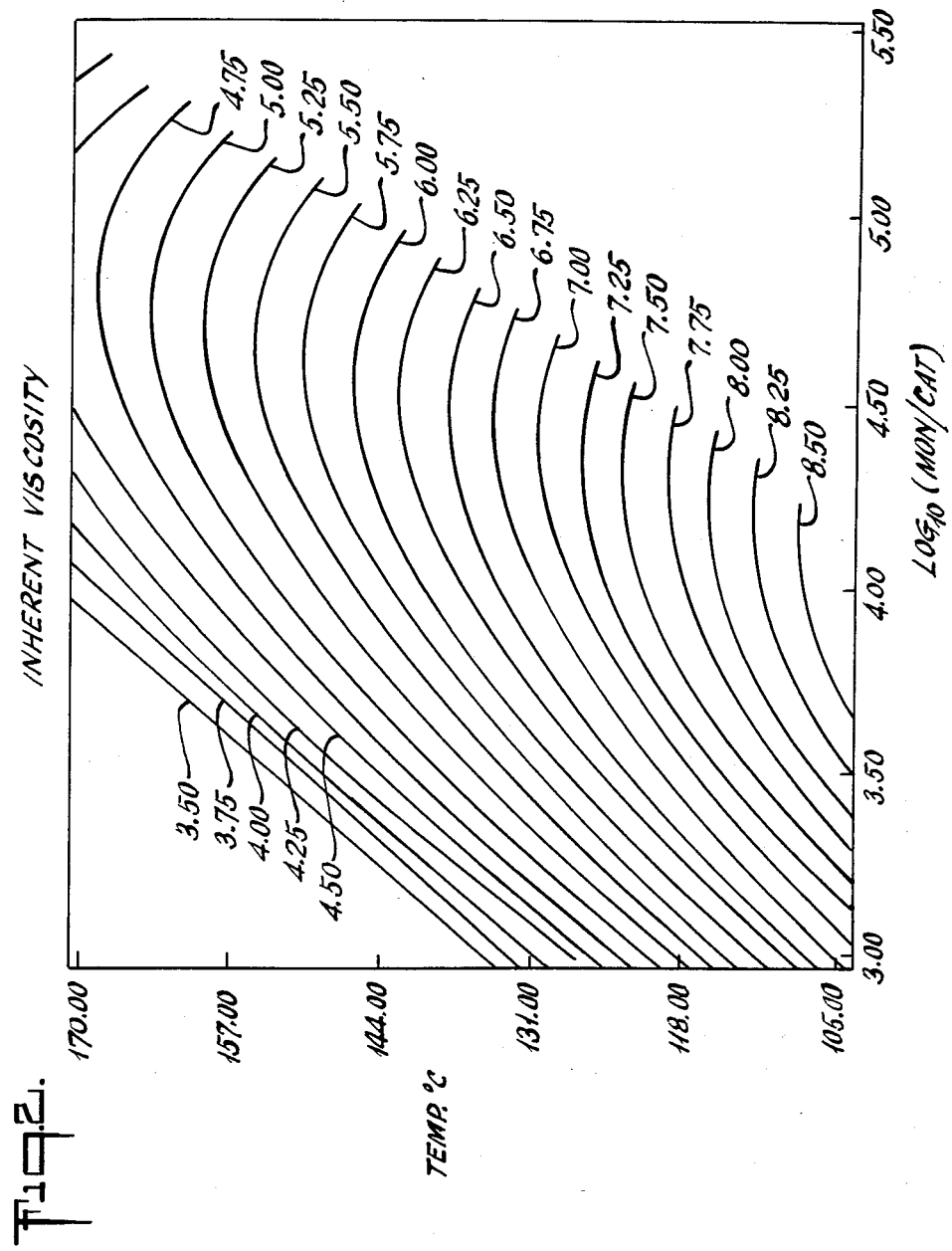
FIG. 2 is a graph plotting inherent viscosities of polymers produced under different reaction conditions.

FIG. 2 shows the polymerization reaction conditions, temperature degrees Celsius versus $\log_{10}$ of the monomer to catalyst ratio showing inherent viscosity of the polymer. The lines in FIG. 2 are lines of constant values of inherent viscosity. The inherent viscosities in FIG. 2 can be defined by the equation:

$$\text{Inherent Viscosity} = 4.45 + 9.18L - 0.207T - 1.51L^2 + 0.032LT.$$

wherein L is the $\log_{10}$ of the monomer to catalyst ratio and T is the temperature in degrees Celsius.

FIG. 3 shows the polymerization reaction conditions in the same manner as FIG. 2 but showing unreacted or residual monomer. The lines in FIG. 2 are constant values of percent unreacted monomer. The percent unreacted monomer can be defined by the equation:

$$\text{Unreacted Monomer} = 28.89 - 15.33L + 6.29L^2 + 0.0026T^2 - 0.213LT$$

wherein L is the $\log_{10}$ of the monomer to catalyst ratio and T is the temperature in degrees Celsius.

The reaction conditions necessary to obtain a polymer with the desired percentage of unreacted monomer and the desired inherent viscosity can be selected from FIG. 1 or from FIGS. 2 and 3.

FIGS. 1, 2 and 3 illustrate the critical relationship between the monomer and catalyst ratio and the temperature of polymerization which must be controlled in order to give the resultant polymer with the necessary properties. In FIG. 1 a monomer to catalyst ratio and a temperature within the boundaries of curve A will generally result in a polymer which will give the necessary load-bearing capability after implantation in the human body. The preferred polymers are those which are made with the polymerization temperature and monomer to catalyst ratios within curve B. These polymers have generally higher inherent viscosities and will maintain tensile strength for longer time periods.

FIG. 2 is a plot of the inherent viscosity of polymers plotted against temperature and the log of the monomer catalyst ratio. The lines that appear in FIG. 2 are lines of constant inherent viscosity for the polymer under the conditions on the axis of the graph. The polymers that would be produced in the upper left hand corner of the graph would have inherent viscosities below 3.5, and the polymers which would be produced under the conditions on the right hand side of the graph would have residual monomer content of greater than 10%.

The plot of FIG. 3 shows the percent residual monomer that would be obtained under various reaction conditions. The lines on FIG. 3 are lines of constant percent residual monomer. The area on the right hand side of the graph would be polymers which contain more than 10% residual monomer. Again, as in FIG. 2, the area in the upper left hand portion of the graph would be conditions that would result in polymers having inherent viscosities of less than 3.5.

By comparing FIGS. 2 and 3, it is possible to select the reaction conditions, temperature and monomer to catalyst ratio to obtain a polymer of the desired inherent viscosity and low residual monomer content.

In the following Examples, the inherent viscosities of the polymers were determined as a 1% solution in chloroform at 25° C. using a Cannon-Fenke Viscometer No. 50.

EXAMPLE 1

Preparation of Polymer

Forty grams of L(−) lactide were charged into a 50 ml. long-neck, round bottom flask. To the flask 0.56 ml. stannous octoate solution (0.33 M in toluene) was added resulting in a monomer/catalyst ratio of 1488. After a magnetic bar was added, the flask was evacuated for 15 minutes to 0.02 mmHg pressure and purged with dry nitrogen. Evacuation and purging was repeated. The flask was evacuated for the third time and then hermetically sealed. The flask was immersed in an oil bath and kept at 105° C. for 66.5 hours. During the initial few hours the contents of the flask were stirred by the magnet. At the end of 66.5 hours, the flask was allowed to cool and was broken. Solid polymer was recovered and stored under vacuum. Inherent viscosity of this polymer was determined to be 5.06.

EXAMPLE 2

Preparation of Polymer

The procedure of Example 1 was used except that the amount of L(−)lactide used in the polymerization was 373 g and the monomer/catalyst ratio was 1413. The polymerization temperature was maintained at 105° C. and the polymerization time was 69.5 hours. The polymer obtained exhibited an inherent viscosity of 5.26 and an intrinsic viscosity of 5.50.

EXAMPLE 3

This example illustrates how the inherent viscosity of poly L(−)lactide is affected by varying the monomer/catalyst ratio. The procedure of Example 1 was used but the amount of L(−)lactide was 300 g in all the batches. The monomer/catalyst ratio and polymerization temperature are summarized in Table I together with the inherent viscosity and the percent of unreacted monomer in the final polymer.

TABLE I

| Polymer | Monomer/Catalyst Ratio | Reaction Temp., °C. | Inherent Viscosity | Unreacted Monomer, % |
|---|---|---|---|---|
| A | 18275 | 105 | 0.30 | 65.8 |
| B | 12400 | 110 | 2.89 | <1 |
| C | 11267 | 105 | 1.63 | 5.7 |
| D | 5208 | 105 | 9.70 | 3.1 |
| E | 1302 | 105 | 6.51 | 0 |
| F | 1413 | 105 | 5.26 | — |
| G | 1488 | 105 | 5.06 | — |
| H | 1488 | 105–168 | 3.49 | — |
| I | 1240 | 110–160 | 2.24 | 0 |
| J | 1127 | 110–230 | 2.15 | 0 |

EXAMPLE 4

This example illustrates the effects of polymerizing L(−) lactide at higher temperatures and at high and low monomer/catalyst ratios.

The procedure used for the polymerization of L(−)lactide is the same as used in Example 1 except for the monomer/catalyst ratios, reaction temperatures and reaction times. The amount of lactide used was 300 gms. for each batch. The results are summarized in Table II.

TABLE II

| Polymer | Monomer/Catalyst Ratio | Reaction Time, Hrs. | Reaction Temp., °C. | Inherent Viscosity | Unreacted Monomer, % |
|---|---|---|---|---|---|
| K | 548246 | 258 | 107–210 | 2.96 | 18.3 |
| L | 289352 | 90 | 150 | 4.66 | 15.0 |
| M | 274123 | 194 | 105–187 | 4.18 | 17.7 |
| N | 260417 | 93 | 163–170 | 4.73 | 0.1–10.0 |
| O | 28935 | 90 | 150 | 5.67 | 1.1 |
| P | 26042 | 41 | 160–181 | 3.60 | 1.2 |
| Q | 2604 | 18 | 155–167 | 2.74 | 0 |

EXAMPLE 5

This example illustrates the rate of shear strength decrease of the polymer of Example 2 in Buffer-7 at 37.8° C. Test specimens were prepared from this polymer in the form of pins, 15 mm long and 3–4 mm in diameter. The results are shown in Table III.

TABLE III

Shear Strength and Hardness As a Function of Time

| Period in Test. Sol. | Diameter (Inch) | Shear Strength (lbs.) | Shear Strength (psi) | Hardness at 0.01 Penet. (lbs.) |
|---|---|---|---|---|
| Dry | 0.196 | 131.0 | 4342 | 27.5 |
| 1 Month | 0.195 | 55.9 | 1872 | 27.6 |
| 2 Months | 0.200 | 12.1 | 385 | 37.0 |
| 3 Months | 0.198 | 6.7 | 212 | 13.6 |

EXAMPLE VI

This example shows the results obtained from a series of polymerization of various monomer catalyst ratios, reaction temperatures and reaction times. Some of the polymers identified in Table IV are also reported in Tables I and II. The data from Table IV has been plotted on FIGS. 1, 2 and 3 to illustrate the conditions that are necessary to produce the high molecular weight polymer of the present invention.

TABLE IV

Variables of the Polymer Synthesis

| Polymer No. | Molar Ratio Monomer/Catalyst | Reaction Temperature °C. | Reaction Time, Hours | Inherent Viscosity | Residual Monomer in the Polymer, % |
|---|---|---|---|---|---|
| 1 | 12400 | 110–160 | 51 | 2.8 | 0 |
| 2 | 1240 | 110–160 | 51 | 2.2 | 0 |
| 3 | 11267 | 105 | 91 | 1.6 | 6.0 |
| 4 | 18275 | 104–105 | 118 | 0.3 | 66.0 |
| 5 | 27412 | 105–183 | 75 | 4.6 | 0 |
| 6 | 26042 | 160–181 | 41 | 3.6 | 1.2 |
| 7 | 2604 | 155–167 | 18 | 2.7 | 0 |
| 8 | 260417 | 163–170 | 93 | 4.7 | 10.0 |
| 9 | 28935 | 150 | 90 | 5.7 | 1.0 |
| 10 | 289352 | 150 | 90 | 4.7 | 15.0 |
| 11 | 5208 | 105 | 66 | 9.7 | 4.4 |
| 12 | 1302 | 105 | 66 | 6.5 | 1.5 |
| 13 | 4963 | 110 | 74 | 9.0 | 1.9 |
| 14 | 5708 | 150 | 74 | 4.5 | 0.6 |
| 15 | 5631 | 110 | 67 | 8.4 | 3.0 |
| 16 | 5631 | 150 | 67 | 3.7 | 0.2 |
| 17 | 11905 | 110–120 | 42 | 8.6 | 1.6 |
| 18 | 5952 | 116–120 | 42 | 8.0 | 1.7 |
| 19 | 2815 | 110 | 65 | 8.3 | 5.0 |
| 20 | 28153 | 120 | 74 | 0.6 | 64.0 |
| 21 | 5631 | 130 | 69 | 7.4 | 0.7 |
| 22 | 5631 | 120 | 69 | 7.2 | 1.0 |
| 23 | 27412 | 130 | 46 | 7.6 | 7.3 |
| 24 | 13706 | 120 | 46 | 8.9 | 1.9 |
| 25 | 2637 | 105–110 | 76 | 7.4 | 7.0 |
| 26 | 1319 | 105–110 | 76 | 7.0 | 1.7 |
| 27 | 2815 | 115 | 52 | 6.8 | 0.7 |
| 28 | 1408 | 110 | 52 | 6.5 | 0.6 |
| 29 | 1447 | 137–139 | 64 | 3.1 | 0 |
| 30 | 4452 | 137–139 | 64 | 4.5 | 0 |
| 31 | 22645 | 137–139 | 64 | 6.5 | 0 |
| 32 | 86806 | 137–139 | 64 | 6.7 | 11.4 |
| 33 | 236742 | 137–139 | 64 | 5.6 | 17.1 |
| 34 | 1353 | 115 | 64.5 | 5.0 | 0 |
| 35 | 2706 | 115 | 64.5 | 6.1 | 0.6 |
| 36 | 20833 | 115 | 64.5 | 7.4 | 2.1 |
| 37 | 86806 | 115 | 64.5 | 5.9 | 28.0 |
| 38 | 236742 | 115 | 64.5 | 0.02 | 98.0 |

EXAMPLE VII

This example shows the effect of the presence of unreacted monomer on the in vitro degradation of the polymer with time. Samples of the polymers identified in Table IV were placed in a Buffer 7 solution at 37° C. The samples were rectangular blocks 20 mm long, 3 mm wide and 1 mm thick. The samples were removed at various times, and the shear strength determined. The results show that the presence of unreacted monomer in the polymer causes the polymer to lose strength at a much faster rate than if the unreacted monomer is not present in the polymer

TABLE V

IN-VITRO SHEAR STRENGTH VS. TIME

| Time in Buffer 7 @ 37° C., weeks | Shear Strength (kg/cm²) Polymer Numbers | | |
|---|---|---|---|
| | 5 | 11 | 8 |
| 0 | 674 | 659 | 530 |
| 1 | 579 | 375 | 341 |
| 2 | 494 | 215 | 197 |
| 3 | 387 | 133 | 115 |
| 4 | 356 | 104 | 64 |
| 6 | 336 | 79 | 49 |
| 8 | 205 | 57 | 42 |
| 10 | 209 | 45 | 23 |
| 12 | 195 | 58 | 42 |
| 16 | 160 | 44 | 28 |
| 20 | 133 | 25 | 19 |
| 24 | 134 | 39 | 18 |
| Unreacted Monomer % | 0 | 4.4 | 10 |

The data in Table V is shown in FIG. 5.

EXAMPLE VIII

This example shows the effect of the molecular weight on the in vitro tensile strength of certain polymers identified in Table IV with time. Samples of each of the polymers were placed in a Buffer 7 solution at 37°

C. The samples were rectangular blocks 20 mm long, 3 mm wide and 1 mm thick. Samples were removed at various times, and the tensile strength determined. The results in Table VI show that a high molecular weight is necessary in order for the polymer to have adequate tensile strength at 8 weeks in vitro.

TABLE VI

IN-VITRO TENSILE STRENGTH

| Duration of Immersion In Buffer 7 @ 37° C., weeks | Tensile Strength, kg/cm$^2$ Polymer Numbers | | |
|---|---|---|---|
| | 21 | 16 | 14 |
| 0 | 582 | 288 | 261 |
| 1 | 553 | — | — |
| 2 | 519 | 243 | 245 |
| 3 | 487 | — | — |
| 4 | 424 | 212 | 170 |
| 6 | 348 | 149 | 153 |
| 8 | 271 | 162 | 92 |
| 10 | 139 | 48 | 51 |
| 12 | 95 | 36 | 23 |
| 16 | 66 | 21 | — |
| Inherent Viscosity | 7.4 | 3.7 | 4.5 |

EXAMPLE IX

Samples of two polymers, 21 and 16 from Table IV, were implanted in the back muscles of rats and removed after varying time periods and tested for tensile strength. The results are shown in Table VII.

TABLE VII

IN-VIVO TENSILE STRENGTH

| Duration of Implantation, weeks | Tensile Strength, kg/cm Polymer Numbers | |
|---|---|---|
| | 21 | 16 |
| 0 | 582 | 288 |
| 2 | 522 | — |
| 4 | — | 92 |
| 6 | 304 | 92 |
| 8 | 224 | 48 |
| 12 | 182 | * |
| 16 | 45 | ** |
| Inherent Viscosity | 7.4 | 3.7 |

*Sample broke during handling.
**Sample was broken when explanted.

The data in the tables of Examples VIII and IX are plotted in FIG. 4. The in vivo and in vitro tensile strength of polymer 2 are similar and are shown in FIG. 4 as a single line. Line 16T in FIG. 4 is the plot of in vitro tensile strength of polymer 16, and line 16V is the plot of the in vivo tensile strength of polymer 16. Polymer 16, although appearing to have the necessary retained tensile strength in the in vitro test line 16T, is clearly not acceptable according to the results of the in vivo test line 16V.

EXAMPLE X

Samples of polymers 9, 5 and 2 of Table IV, in the form of rectangles 20 mm long, 3 mm wide and 1 mm thick, were tested for in vitro and in vivo shear strength. In the in vitro test, the samples were placed in Buffer-7 at 37° C. and individual samples were removed and tested for shear strength after varying time periods. In the in vivo test, the samples were implanted in the back muscles of rats, removed and tested for shear strength.

Figure 6:
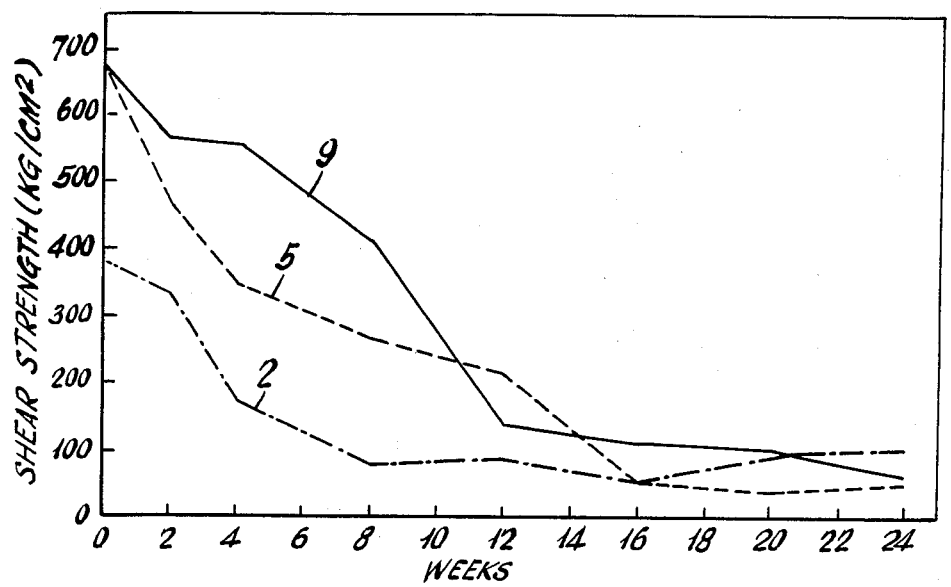
FIGS. 6 and 7 are graphs plotting the loss of shear strength with time of various lactide polymers, FIG. 6 being in vivo and FIG. 7 being in vitro.
Figure 7:
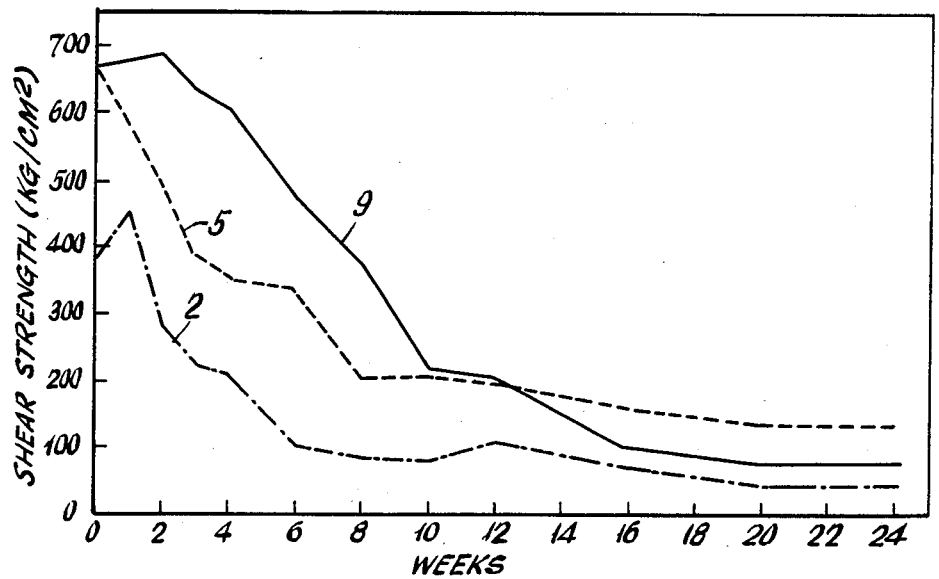

The results of the in vivo test are shown in FIG. 6, and the results of the in vitro test are shown in FIG. 7.

The preceding Examples illustrate the necessity of controlling the polymerization conditons in order to obtain polymers which can be formed into bone fixation devices with the strength necessary to function in the body.

I claim:

1. A process of forming a high molecular weight polyactide polymer capable of being used as a resorbable bone fixation device comprising:
   polymerizing L(—)lactide monomer in an inert atmosphere in the presence of a stannous octoate catalyst,
   said catalyst being present in a monomer to catalyst mole ratio of from 1000 to 300,000,
   the polymerization being conducted at a temperature of from 105° C. to 170° C.,
   the temperature and monomer to catalyst mole ratio being selected to fall within the curve A of FIG. 1 to form a polymer having an unreacted monomer content of less than 2% and an inherent viscosity as a 1 percent solution in chloroform at 25° C. of between 4.5 and 10.

2. The process of claim 1 in which the temperature of polymerization and the monomer to catalyst mole ratio are selected to fall within curve B of FIG. 1.

3. The process of claim 1 in which the monomer to catalyst mole ratio is between 1,100 and 45,000 and the temperature of polymerization is between 105° C. and 155° C.

4. The process of claim 1 in which the monomer to catalyst mole ratio is between 1,300 and 20,000 and the temperature of polymerization is between 110° C. and 130° C.

5. A process of forming a high molecular weight polylactide polymer capable of being used as a resorbable bone fixation device comprising:
   polymerizing L(—)lactide monomer in an inert atmosphere in the presence of a stannous octoate catalyst,
   said catalyst being present in a monomer to a catalyst mole ratio of from 1,000 to 300,000,
   the polymerization being conducted at a temperature of from 110° C. to 170° C.,
   the temperature and monomer to catalyst mole ratio being selected so that the inherent viscosity of the polymer as a 1 percent solution in chloroform at 25° C. is between 4.5 and 10 and satisfies the equation, inherent viscosity = $(4.45 + 9.18L - 0.207T - 1.51L^2 + 0.032LT)$ and the unreacted monomer content of the polymer is less than 2% based on the total weight of reaction product and satisfies the equation, unreacted monomer = $(28.89 - 15.33L + 6.29L^2 + 0.0026T^2 - 0.213LT)$ wherein L is the log to the base 10 of the monomer to catalyst mole ratio and T is the temperature in degrees Celsius.

6. The process of claim 5 in which the monomer to catalyst mole ratio is between 1,100 and 45,000 and the temperature of polymerization is between 105° C. and 155° C.

7. The process of claim 5 in which the catalyst is present in a monomer to catalyst mole ratio of from 1,300 to 20,000 and the temperature of polymerization is between 110° C. and 130° C.

* * * * *